US011364208B2

(12) United States Patent
Mendrok-Edinger et al.

(10) Patent No.: US 11,364,208 B2
(45) Date of Patent: Jun. 21, 2022

(54) TOPICAL COMPOSITIONS

(71) Applicant: DSM IP ASSETS B.V., Heerlen (NL)

(72) Inventors: Christine Mendrok-Edinger, Kaiseraugst (CH); Sebastien Mongiat, Kaiseraugst (CH); Thomas Rudolph, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 141 days.

(21) Appl. No.: 16/628,434

(22) PCT Filed: Jun. 28, 2018

(86) PCT No.: PCT/EP2018/067365
§ 371 (c)(1),
(2) Date: Jan. 3, 2020

(87) PCT Pub. No.: WO2019/007789
PCT Pub. Date: Jan. 10, 2019

(65) Prior Publication Data
US 2020/0163905 A1    May 28, 2020

(30) Foreign Application Priority Data
Jul. 6, 2017   (EP) .................................. 17180054

(51) Int. Cl.
*A61K 31/12* (2006.01)
*A61P 17/10* (2006.01)
(Continued)

(52) U.S. Cl.
CPC .............. *A61K 31/12* (2013.01); *A61K 8/042* (2013.01); *A61K 8/062* (2013.01); *A61K 8/064* (2013.01);
(Continued)

(58) Field of Classification Search
CPC .. A61K 2300/00; A61K 31/121; A61K 31/12; A61K 8/35; A61K 31/381; A61K 31/44; A61K 31/505; A61K 31/513; A61K 8/062; A61K 8/60; A61K 8/042; A61K 8/064; A61K 9/0014; A61K 31/047; A61K 9/107; A61K 2800/5922; A61K 31/4155; A61K 45/06; A61K 8/345; A61K 8/498; A61K 8/9789; A61K 9/0031; A61K 9/0034; A61K 31/05; A61K 36/28; A61K 36/67; A61K 36/81; A61K 36/9068; A61K 47/10; A61K 47/22; A61K 47/26; A61K 47/32; A61K 8/37; A61K 8/922; A61K 2800/49; A61K 2800/52; A61K 2800/524; A61K 2800/592; A61K 2800/74; A61K 8/046; A61K 8/342; A61K 8/375; A61K 8/4973; A61K 8/891; A61K 8/97; A61K 8/9728; A61K 8/9783; A61K 8/9794; A61K 9/1271; A61K 2800/10; A61K 2800/31; A61K 2800/56; A61K 2800/75; A61K 2800/874; A61K 31/01; A61K 31/198; A61K 31/22; A61K 31/225; A61K 31/23; A61K 31/232; A61K 31/235; A61K 31/355; A61K 31/357; A61K 31/415; A61K 31/425; A61K 31/515; A61K 36/886; A61K 47/02; A61K 47/08; A61K 47/12; A61K 47/14; A61K 47/18; A61K 47/34; A61K 47/36; A61K 8/022; A61K 8/33; A61K 8/347; A61K 8/40; A61K 8/411; A61K 8/585; A61K 8/602; A61K 8/64; A61K 8/676; A61K 8/732; A61K 9/06; A61K 9/1617; A61K 9/1623; A61K 9/1652; A61K 9/1658; A61K 8/86; A61K 8/26; A61K 8/731; A61K 31/695; A61K 8/28; A61K 8/39; A61K 9/122; A61K 8/0208; A61K 8/31; A61K 8/8158; A61K 8/87; A61K 8/894; A61K 9/1075; A61K 9/12; A61K 2800/30; A61K 31/70; A61K 35/02; A61K 36/14; A61K 36/17; A61K 36/185; A61K 36/24; A61K 36/48; A61K 36/53; A61K 36/704; A61K 36/71; A61K 47/06; A61K 47/38; A61K 47/44; A61K 8/19; A61K 8/27; A61K 8/44; A61K 8/733; A61K 2800/21; A61K 2800/24; A61K 2800/242; A61K 2800/244; A61K 2800/413; A61K 2800/70; A61K 2800/91; A61K 31/015; A61K 31/07; A61K 31/137; A61K 31/155; A61K 31/167; A61K 31/17; A61K 31/19; A61K 31/196; A61K 31/20; A61K 31/202; A61K 31/203;
(Continued)

(56) References Cited
FOREIGN PATENT DOCUMENTS

| CN | 105188660 | 12/2015 |
|---|---|---|
| DE | 10 2008 031 556 | 4/2009 |

(Continued)

OTHER PUBLICATIONS

Myriam Elseviers et al., "A sweet tooth? Dental plaque and the use of anti-cariogenic sweeteners", Agro-Food-Industry Hi-Tech, Teknoscience, Jan. 1, 2000, pp. 24-29.
(Continued)

*Primary Examiner* — Audrea B Coniglio
(74) *Attorney, Agent, or Firm* — Nixon & Vanderhye P.C.

(57) ABSTRACT

The present invention relates to topical compositions comprising erythrulose and hydroxyacetophenone as well as the use thereof for the prevention and/or treatment of ailments associated with *Malassezia* yeast, *Propionibacterium acnes* as well as the protection against molds such as in particular *Aspergillus brasiliensis*.

17 Claims, No Drawings

(51) Int. Cl.
*A61P 31/10* (2006.01)
*A61K 8/04* (2006.01)
*A61K 8/06* (2006.01)
*A61K 8/35* (2006.01)
*A61K 9/107* (2006.01)
*A61Q 5/02* (2006.01)
*A61Q 5/12* (2006.01)
*A61Q 17/00* (2006.01)
*A61Q 19/00* (2006.01)

(52) U.S. Cl.
CPC .............. *A61K 8/35* (2013.01); *A61K 9/107* (2013.01); *A61P 17/10* (2018.01); *A61P 31/10* (2018.01); *A61Q 5/02* (2013.01); *A61Q 5/12* (2013.01); *A61Q 17/005* (2013.01); *A61Q 19/00* (2013.01); *A61K 2800/5922* (2013.01)

(58) Field of Classification Search
CPC .. A61K 31/351; A61K 31/41; A61K 31/4164; A61K 31/4174; A61K 31/433; A61K 31/436; A61K 31/4412; A61K 31/4422; A61K 31/496; A61K 31/497; A61K 31/506; A61K 31/52; A61K 31/522; A61K 31/535; A61K 31/5375; A61K 31/551; A61K 31/554; A61K 31/56; A61K 31/567; A61K 31/568; A61K 31/573; A61K 31/575; A61K 31/7036; A61K 31/7048; A61K 35/04; A61K 36/00; A61K 38/00; A61K 38/12; A61K 38/13; A61K 38/212; A61K 45/00; A61K 47/20; A61K 47/24; A61K 47/46; A61K 8/06; A61K 8/068; A61K 8/34; A61K 8/361; A61K 8/362; A61K 8/365; A61K 8/42; A61K 8/4926; A61K 8/494; A61K 8/4953; A61K 8/4993; A61K 8/671; A61K 8/73; A61K 8/736; A61K 8/737; A61K 8/8141; A61K 8/8147; A61K 8/8152; A61K 8/8176; A61K 8/965; A61K 8/9717; A61K 8/9761; A61K 8/9767; A61K 8/9771; A61K 9/0007; A61K 9/006; A61K 9/10; A61K 9/124; A61K 9/7015; C08F 220/603; C08F 230/06; C08F 220/56; C08F 8/12; C08F 8/28; C08F 120/60; C08F 120/56; C08F 130/06; C08F 220/60; C08F 2800/10; C08F 2810/50; A61Q 19/00; A61Q 5/02; A61Q 5/12; A61Q 17/005; A61Q 17/04; A61Q 19/10; A61Q 5/006; A61Q 19/04; A61Q 19/02; A61Q 5/00; A61Q 15/00; A61Q 17/00; A61Q 19/005; A61Q 19/002; A61Q 19/004; A61Q 19/08; A61Q 5/06; A61Q 7/00; A61Q 17/02; A61Q 19/06; A61Q 5/008; A61Q 19/007; A61Q 19/008; A61Q 5/004; A61Q 5/04; A61Q 7/02; A61P 17/00; A61P 17/10; A61P 31/10; A61P 43/00; A61P 29/00; A61P 11/00; A61P 11/02; A61P 11/06; A61P 13/12; A61P 17/04; A61P 17/06; A61P 17/16; A61P 19/02; A61P 1/00; A61P 1/04; A61P 25/00; A61P 27/02; A61P 31/18; A61P 37/02; A61P 37/06; A61P 37/08; A61P 3/10; A61P 9/00; A61P 9/10; A61P 17/02; A61P 17/08; A61P 31/00; A61P 31/04; A61P 31/12; A61P 33/00; A61P 35/00; A61P 13/00; A61P 15/00; A61P 15/02; A61P 17/14; A61P 19/00; A61P 19/08; A61P 23/00; A61P 27/14; A61P 27/16; A61P 37/00; A61P 5/00; A61P 5/38; C11D 17/042; C11D 17/043; C11D 17/044; C11D 3/505; C11D 3/2093; C11D 3/222; C11D 3/225; C11D 3/3761; C11D 3/378; C11D 3/38; C11D 3/386; C11D 3/38609; C11D 3/38627; C11D 3/38636; C11D 3/38645; A23L 2/52; A23L 33/10; A23L 27/204; A23L 27/00; A23L 27/2054; A23L 27/36; A23L 2/385; A23L 2/60; A23L 27/20; A23L 27/2052; A23L 27/2056; A23L 27/30; A23L 27/80; A23L 27/86; A23L 27/88; A23L 2/56; A01N 53/00; A01N 65/12; A01N 43/30; A01N 57/12; A01N 65/08; A01N 25/16; A01N 65/00; A01N 2300/00; A01N 25/04; A01N 25/06; A01N 31/02; A01N 37/04; A01N 43/36; A01N 43/40; A01N 43/50; A01N 47/44; A01N 65/28; A01N 25/02; A01N 25/30
See application file for complete search history.

(56) References Cited

FOREIGN PATENT DOCUMENTS

| DE | 102008031556 A1 | * | 4/2009 | ........... A61K 31/135 |
|---|---|---|---|---|
| EP | 0 221 728 | | 5/1987 | |
| EP | 2 774 481 | | 9/2014 | |
| EP | 2774481 A1 | * | 9/2014 | ............. A01N 35/04 |
| WO | 2009/007307 | | 1/2009 | |

OTHER PUBLICATIONS

International Search Report for PCT/EP2018/067365 dated Sep. 18, 2018, 4 pages.
Written Opinion of the ISA for PCT/EP2018/067365 dated Sep. 18, 2018, 6 pages.
First CN Office Action with English-language Translation, CN Appln No. 201880044813.7, dated Feb. 7, 2022.

* cited by examiner

TOPICAL COMPOSITIONS

This application is the U.S. national phase of International Application No. PCT/EP2018/067365 filed Jun. 28, 2018 which designated the U.S. and claims priority to EP Application No. 17180054.3 filed Jul. 6, 2017, the entire contents of each of which are hereby incorporated by reference.

The present invention relates to topical compositions comprising erythrulose and hydroxyacetophenone as well as the use thereof for the prevention and/or treatment of ailments associated with *Malassezia* yeast or *Propionibacterium acnes* as well as the protection thereof against molds such as in particular *Aspergillus brasiliensis*.

To protect cosmetic compositions, household products, plastics, paper and/or paints against mold and bacteria, most products currently on the market contain preservatives. While these preservatives protect against bacteria and fungi, studies have linked daily exposure to many of these substances to an increased risk of skin irritation, cancer and/or endocrine problems. Thus, many manufactures are searching for alternative antimicrobial actives which allow reducing the amount of preservatives and don't appear to pose any health risks.

Antimicrobial active compounds furthermore play a key role for many cosmetic applications:

The fungal genus *Malassezia* comprises lipid-dependent and lipophilic yeast species that are part of the normal skin microbiota. In general, because of their dependence on lipids for survival, *Malassezia* yeasts are most often found in sebum-rich areas of the skin such as the trunk, back, face, and scalp. Several adverse skin conditions have been associated with an overpopulation of *Malassezia* yeasts such as itching skin, *pityriasis versicolor*, dandruff formation, seborrheic dermatitis atopic dermatitis, and psoriasis.

During dandruff, for example, the levels of *Malassezia* increase by 1.5 to 2 times of its normal level. Penetration triggered by oleic acid through the top layer of the epidermis, the stratum corneum, results in an inflammatory response in susceptible persons which disturbs homeostasis and results in erratic cleavage of stratum corneum cells.

*Malassezia* overpopulations are often treated with topical antifungal agents such as azole antifungal drugs, which however may have severe side effect such as e.g. sensitization reactions, skin irritation reactions or the formation of potentially resistant strains.

Thus, there is an ongoing need for mild treatments for the reduction of *Malassezia* yeast populations on the skin of humans and animals which are well tolerated by the skin in order to maintain a healthy homeostasis of the skin and/or improve the health of the skin microbiome and thus alleviate itching of the treated skin and/or scalp area.

Furthermore, there is a need for the mild preservation of topical compositions such as cosmetic or pharmaceutical products against *Aspergillus brasiliensis*.

Surprisingly it has now been found that erythrulose, a well-accepted cosmetic ingredient synergistically enhances the antimicrobial activity of hydroxyacetophenone against *Malassezia furfur*. Thus, the combination can effectively be used to control the *Malassezia* population on the skin and/or the scalp and thus overcome the adverse effects resulting from a *Malassezia furfur* overpopulation on the skin and/or scalp such as itching skin.

Furthermore, it has been found that erythrulose and hydroxyacetophenone excerpt a synergistic antimicrobial activity against *Aspergillus brasiliensis* (*A. brasiliensis*). Thus, the combination is particularly suitable to protect topical compositions against microbial contamination respectively decay caused by *A. brasiliensis*.

Thus, in a first embodiment the present invention relates to topical compositions comprising erythrulose and hydroxyacetophenone.

In another embodiment, the invention relates to the use of a combination of erythrulose and hydroxyacetophenone as antimicrobial agent against *Malassezia* yeasts such as in particular *Malassezia furfur* and/or molds such as in particular *Aspergillus brasiliensis*.

In a further embodiment, the invention relates to a method for killing and/or inhibiting the growth of *Malassezia* yeasts, such as preferably *Malassezia furfur*, *Propionibacterium acnes* and/or molds such as preferably *Aspergillus brasiliensis*, said method comprising contacting said yeasts, *Propionibacterium acnes* respectively molds with a combination (mixture) of erythrulose and hydroxyacetophenone.

Due to the antimicrobial activity against *Malassezia* yeasts the combination of erythrulose and hydroxyacetophenone is further suitable for the treatment of adverse skin conditions associated with an overpopulation of such yeasts by maintaining skin homeostasis and/or improving the health of the skin microbiome.

Thus, the invention also relates to a method of treating the skin and/or the scalp, said method comprising the steps of contacting the skin and/or scalp with a topical composition comprising erythrulose and hydroxyacetophenone, in particular for the treatment, prevention and/or prophylaxis of itching skin as well as for maintaining skin homeostasis and/or skin microbiome balance.

In a further embodiment, the present invention relates to the use of a topical composition comprising erythrulose and hydroxyacetophenone for the treatment, prevention and/or prophylaxis of itching skin as well as for maintaining skin homeostasis and/or skin microbiome balance.

Further suitable uses of the topical compositions according to the present invention encompass pharmaceutical applications. Thus, the topical compositions according to the present invention may be used for the treatment, prevention and/or prophylaxis of any disorder and disease where it is desirable to kill and/or inhibit the growth of *Malassezia* yeasts such as in particular *Malassezia furfur* in a patient in need thereof such as e.g. for the treatment, prevention and/or prophylaxis of *pityriasis versicolor*, dandruff formation, seborrheic dermatitis, atopic dermatitis and psoriasis.

Due to the antimicrobial activity against *Propionibacterium acnes* the combination of erythrulose and hydroxyacetophenone is further suitable for the treatment of adverse skin conditions associated with an overpopulation of such *Propionibacterium acnes* by maintaining skin homeostasis and/or improving the health of the skin microbiome.

Another suitable use of the topical composition according to the present invention is the treatment, prevention and/or prophylaxis of acne as the combination is also highly effective in killing/inhibiting the growth of *Propionibacterium acnes* (*P. acnes*).

The term "erythrulose" refers to erythrulose in D- or L-form or as the racemate. Preferably L-(+)-Erythrulose [533-50-6] is used. Erythrulose is e.g. commercially available at DSM Nutritional Products Ltd, Kaiseraugst.

The term hydroxyacetophenone refers to o-, m- or p-hydroxyacetophenone. Particularly preferred in all embodiments of the present invention is p-hydroxyacetophenone [CAS 99-93-4] which is also called 1-(4-hydroxyphenyl)-ethanone and which is e.g. commercially available at Symrise as SymSave® H.

The term "antimicrobial activity" (or "antimicrobial effect") as used herein means a capability of killing and/or inhibiting the growth of *Malassezia* yeasts such as in particular *Malassezia furfur, Propionibacterium acnes* and/or molds such as *Aspergillus brasiliensis*.

In all embodiments of the present invention preferably the topical compositions do not contain (are substantially free of) any ingredient with a primary or secondary amino group selected from primary or secondary aromatic amines or nitrogen containing heterocyclic compounds.

In all embodiments of the present invention the topical compositions preferably comprise erythrulose in an amount selected in the range of about 0.005 to 5 wt.-%, more preferably in the range of about 0.01 to 3 wt.-% and most preferably in the range of 0.025 to 2 wt.-%, such as in an amount of 0.04 to 1 wt.-% and particularly advantageously in an amount of 0.04 to 0.75 wt.-%, such as in an amount of 0.04 to 0.5 wt.-%, based on the total weight of the composition. Further particular suitable ranges include 0.01 to 0.2 wt.-% or 0.05 to 0.2 wt.-%, in particular for the selective treatment *M. furfur, P. acnes* and/or *A. Brasiliensis*.

In all embodiments of the present invention the topical compositions preferably comprise hydroxyacetophenone in an amount selected in the range of about 0.01 wt.-% to 2 wt.-%, preferably in the range of 0.1 wt.-% to 1 wt.-%, most preferably in the range of 0.1 wt.-% to 0.6 wt.-%, based on the total weight of the composition.

Preferably, in all embodiments of the present invention, the ratio (w/w) of erythrulose to hydroxyacetophenone is selected in the range of about 10:1 to 0.1:1, more advantageously in the range of about 5:1 to 0.5:1. Further particular suitable ranges include 0.01 to 0.2 wt.-% or 0.05 to 0.2 wt.-%.

To make use of the anti-microbial activity against *Malassezia* yeasts, *P. acnes* respectively *Aspergillus brasiliensis* of the combination of erythrulose and hydroxyacetophenone, it can be used in a multiplicity of formulations or applications, such as, for example, cosmetic or pharmaceutical compositions, medicinal products or household products.

In particular the present invention relates to the use of a mixture of erythrulose and hydroxyacetophenone for improving preservation, in particular of a product selected from the group of cosmetic compositions, household products, plastics, paper and/or paints compared to the product not containing erythrulose and optionally appreciating the effect, preferably in view of *Aspergillus brasiliensis*.

Thus, in another embodiment, the invention relates to a method of preventing microbial decay and breakdown in particular caused by molds such as most in particular by *Aspergillus brasiliensis* of cosmetic and/or pharmaceutical compositions, household products, plastics, paper and/or paints, wherein said method comprises adding to the compositions, products, plastics, papers and/or paints a combination (mixture) of erythrulose and hydroxyacetophenone with all the definitions and preferences as given herein. In a particular embodiment, the method also encompasses the step of appreciating the result.

In a particular advantageous embodiment, the invention relates to a method of preventing microbial decay and breakdown of cosmetic or pharmaceutical compositions in particular caused by molds such as most in particular by *Aspergillus brasiliensis*, which compositions (next to the combination (mixture) of erythrulose and hydroxyacetophenone) furthermore comprise water and at least one further agent selected from the group consisting of surfactants, emulsifiers, thickeners, and oils as such compositions are particular sensitive to microbial growth.

Thus, in another embodiment, the invention is also directed to cosmetic or pharmaceutical compositions comprising water and at least one agent selected from the group consisting of surfactants, emulsifiers, thickeners and oils, wherein the composition furthermore comprises the mixture of erythrulose and hydroxyacetophenone with all the definitions and preferences as given herein.

The use according to the invention of the combination of erythrulose and hydroxyacetophenone can take place both in the cosmetic sense as well as in the pharmaceutical sense. A pharmaceutical application is conceivable, for example, in the case of anti-dandruff compositions. In all embodiments of the present invention, the use is however preferably cosmetic (non-therapeutic) such as against itching skin or maintenance of skin homeostasis.

The topical compositions according to the present invention are preferably cosmetic or pharmaceutical compositions which are topically applied to mammalian keratinous tissue such as in particular to human skin or the human scalp and hair.

The term "cosmetic composition" as used in the present application refers to cosmetic compositions as defined under the heading "Kosmetika" in Rompp Lexikon Chemie, 10th edition 1997, Georg Thieme Verlag Stuttgart, New York as well as to cosmetic compositions as disclosed in A. Domsch, "Cosmetic Compositions", Verlag für chemische Industrie (ed. H. Ziolkowsky), $4^{th}$ edition, 1992.

The cosmetic or pharmaceutical compositions according to the present invention preferably further comprise a physiologically acceptable medium, that is to say a medium compatible with keratinous substances, such as the skin, mucosa, and keratinous fibers. Preferably, the physiologically acceptable medium is a cosmetically or pharmaceutically acceptable carrier.

The term cosmetically or pharmaceutically acceptable carrier refers to all carriers and/or excipients and/or diluents conventionally used in cosmetic compositions.

The topical compositions according to the present invention are generally prepared by admixing erythrulose and hydroxyacetophenone in the amounts indicated herein with a suitable carrier.

The exact amount of carrier will depend upon the actual level of erythrulose and hydroxyacetophenone and any other optional ingredients that one of ordinary skill in the art would classify as distinct from the carrier (e.g., other active ingredients). In an advantageous embodiment, the cosmetic or pharmaceutical compositions according to the present invention comprise from about 50% to about 99%, preferably from about 60% to about 98%, more preferably from about 70% to about 98%, such as in particular from about 80% to about 95% of a carrier, based on the total weight of the cosmetic composition.

In a particular advantageous embodiment, the carrier consists furthermore of at least 40 wt.-%, more preferably of at least 50 wt.-%, most preferably of at least 55 wt.-% of water, such as in particular of about 55 to about 90 wt.-% of water.

The compositions of the invention (including the carrier) may comprise conventional adjuvants and additives, such as preservatives/antioxidants, fatty substances/oils, organic solvents, silicones, thickeners, softeners, emulsifiers, antifoaming agents, aesthetic components such as fragrances, surfactants, fillers, anionic, cationic, nonionic or amphoteric polymers or mixtures thereof, propellants, acidifying or basifying agents, dyes, colorings/colorants, abrasives, absorbents, chelating agents and/or sequestering agents, essential oils, skin sensates, astringents, pigments or any other ingredients usually formulated into such compositions.

In accordance with the present invention, the compositions according to the invention may also comprise further cosmetically active ingredients conventionally used in cosmetic or pharmaceutical compositions. Exemplary active ingredients encompass skin lightening agents; UV-filters, agents for the treatment of hyperpigmentation;

agents for the prevention or reduction of inflammation; firming, moisturizing, soothing, and/or energizing agents as well as agents to improve elasticity and skin barrier.

Examples of cosmetic excipients, diluents, adjuvants, additives as well as active ingredients commonly used in the skin care industry which are suitable for use in the cosmetic compositions of the present invention are for example described in the International Cosmetic Ingredient Dictionary & Handbook by Personal Care Product Council (http://www.personalcarecouncil.org/), accessible by the online INFO BASE (http://online.personalcarecouncil.org/jsp/Home.jsp), without being limited thereto.

The necessary amounts of the active ingredients as well as the excipients, diluents, adjuvants, additives etc. can, based on the desired product form and application, easily be determined by the skilled person. The additional ingredients can either be added to the oily phase, the aqueous phase or separately as deemed appropriate.

The cosmetically active ingredients useful herein can in some instances provide more than one benefit or operate via more than one mode of action.

Of course, one skilled in this art will take care to select the above mentioned optional additional ingredients, adjuvants, diluents and additives and/or their amounts such that the advantageous properties intrinsically associated with the combination in accordance with the invention are not, or not substantially, detrimentally affected by the envisaged addition or additions.

Preferably, the cosmetic or pharmaceutical compositions according to the invention are in the form of a suspension or dispersion in solvents or fatty substances, or alternatively in the form of an emulsion or micro emulsion (in particular of O/W- or W/O-type), PIT-emulsion, nano emulsion, multiple emulsion (e. g. O/W/O- or W/O/W-type), pickering emulsion, hydrogel, lipogel, one- or multiphase solution or vesicular dispersion.

The cosmetic or pharmaceutical compositions in accordance with the invention can be in the form of a liquid, lotion, a thickened lotion, a gel, a cream, a milk, an ointment or a paste.

The cosmetic or pharmaceutical compositions according to the invention have a pH in the range of 3-10, preferably in the range of pH of 3-8, most preferred in the range of pH 3-6.5. The pH is adjusted by methods known to a person skilled in the art, e.g. by using an acid such as a hydroxy acid including glycolic acid, lactic acid, malic acid, citric acid and tartaric acid or a base such as e.g. sodium or potassium hydroxide or ammonium hydroxide as well as mixtures thereof.

Preferably, in the compositions according to the invention citric acid in an amount of at least 0.0001 wt.-%, such as e.g. in an amount of 0.01-1 wt.-%, in particular in an amount of 0.01 to 0.5 wt.-% is used for pH adjustment.

The cosmetic compositions according to the present invention advantageously comprise a preservative. Particular suitable preservatives in all embodiments of the present invention are phenoxyethanol and ethylhexylglycerin as well as mixtures thereof. When present, the preservative is preferably used in an amount of 0.01 to 2 wt.-%, more preferably in an amount of 0.05 to 1.5 wt.-%, most preferably in an amount of 0.1 to 1.0 wt.-%, based on the total weight of the composition.

The cosmetic compositions according to the present invention are in particular skin care preparations, functional preparations and/or hair care preparations such as most in particularly skin or hair care preparations.

Examples of skin care preparations are, in particular, light protective preparations, anti-ageing preparations, preparations for the treatment of photo-ageing, body oils, body lotions, body gels, treatment creams, skin protection ointments, moisturizing preparations such as moisturizing gels or moisturizing sprays, face and/or body moisturizers, as well as skin lightening preparations.

Examples of functional preparations are cosmetic compositions containing active ingredients such as hormone preparations, vitamin preparations, vegetable extract preparations, anti-ageing preparations, and/or antimicrobial (antibacterial or antifungal) preparations without being limited thereto.

Examples hair care preparations which are suitable according to the invention and which may be mentioned are shampoos, hair conditioners (also referred to as hair rinses), hairdressing compositions, hair tonics, hair regenerating compositions, hair lotions, water wave lotions, hair sprays, hair creams, hair gels, hair oils, hair pomades or hair brilliantines. Accordingly, these are always preparations which are applied to the hair and the scalp for a shorter or longer time depending on the actual purpose for which they are used.

If the hair care preparations according to the invention are supplied as shampoos, these can be clear liquids, opaque liquids (with pearly luster effect), in cream form, gel-like or else in powder form or in tablet form, and as aerosols. The surfactant raw materials on which these shampoos are based can be anionic, cationic, nonionic and amphoteric in nature and also be present in combinations of these substances.

Examples of anionic surfactants suitable for the incorporation into the shampoo preparations according to the present invention are $C_{10-20}$ alkyl- and alkylenecarboxylates, alkyl ether carboxylates, fatty alcohol sulfates, fatty alcohol ether sulfates, alkylolamide sulfates and sulfonates, fatty acid alkylolamide polyglycol ether sulfates, alkanesulfonates and hydroxyalkanesulfonates, olefinsulfonates, acyl esters of isothionates, alpha-sulfo fatty acid esters, alkylbenzenesulfonates, alkylphenol glycol ether sulfonates, sulfosuccinates, sulfosuccinic monoesters and diesters, fatty alcohol ether phosphates, protein-fatty acid condensation products, alkyl monoglyceride sulfates and sulfonates, alkyl glyceride ether sulfonates, fatty acid methyltaurides, fatty acid sarcosinates, and sulforicinoleates. These compounds and their mixtures are used in the form of their salts which are soluble in water or dispersible in water, for example the sodium, potassium, magnesium, ammonium, mono-, di- and triethanolammonium and analogous alkylanunonium salts.

Examples of suitable cationic surfactants are quaternary ammonium salts such as di($C_{10}$-$C_{24}$alkyl)dimethylammonium chloride or bromide, preferably di ($C_{12}$-$C_{18}$alkyl)-dimethylammonium chloride or bromide; $C_{10}$-$C_{24}$-alkyldimethylethylammonium chloride or bromide; $C_{10}$-$C_{24}$-alkyltrimethylammonium chloride or bromide, preferably cetyltrimethylammonium chloride or bromide and $C_{20}$-$C_{24}$-alkyltrimethylammonium chloride or bromide; $C_{10}$-$C_{24}$4-alkyldimethylbenzylammonium chloride or bromide, preferably $C_{12}$-$C_{18}$-alkyldimethylbenzylammoniumchloride; N—($C_{12}$-$C_{18}$-alkyl)pyridinium chloride or bromide, preferably N—($C_{12}$-$C_{16}$-alkyl) pyridinium chloride or bromide; N—($C_{12}$-$C_{18}$-alkyl)isoquinolinium chloride, bromide or monoalkyl sulfate; N—($C_{12}$-$C_{18}$-alkyloylcolaminoformylmethyl)pyridinium chloride; N—($C_{12}$-$C_{18}$-alkyl)-N-methylmorpholinium chloride, bromide or monoalkyl sulfate; N—($C_{12}$-$C_{18}$-alkyl)-N-ethylmorpholinium chloride, bromide or monoalkyl sulfate; $C_{16}$-$C_{18}$-alkylpentaoxethylammonium chloride; isobutylphenoxyethoxyethyldimethyl-benzylammonium chloride; salts of N,N-diethylaminoethylstearylamide and oleylamide with hydrochloric acid, acetic acid, lactic acid, citric acid, phosphoric acid; N-acylamidoethyl-N,N-diethyl-N-methylammonium chloride, bromide or monoalkylsulfate and N-acylaminoethyl-N,N-diethyl-N-benzylammonium chloride, bromide or monoalkyl sulfate, where acyl is preferably stearyl or oleyl.

Examples of suitable nonionic surfactants which can be used as detergent substances are fatty alcohol ethoxylates (alkylpolyethylene glycols); alkylphenol polyethylene glycols; alkyl mercaptan polyethylene glycols; fattyamine ethoxylates (alkylaminopolyethylene glycols); fatty acid ethoxylates (acylpolyethylene glycols); polypropylene glycol ethoxylates (Pluronic); fatty acid alkylolamides (fatty acid amide polyethylene glycols); sucrose esters; sorbitol esters and polyglycol ether.

Examples of amphoteric surfactants which can be added to the shampoos are N—($C_{12}$-$C_{18}$-alkyl)-.beta.-aminopropionates and N—($C_{12}$-$C_{18}$-alkyl)-.beta.-iminodipropionates as alkali metal and mono-, di- and trialkylammonium salts; N-acylamidoalkyl-N,N-dimethylacetobetaine, preferably N—($C_8$-$C_{18}$-acyl)amidopropyl-N, N-dimethylacetobetaine; $C_{12}$-$C_{18}$-alkyldimethylsulfopropylbetaine; amphoteric surfactants based on imidazoline (commercial name: Miranol®, Steinapon®), preferably the sodium salt of 1-(β-carboxymethyloxyethyl)-1-(carboxymethyl)-2-laurylimidazolinium; amine oxide, for example $C_{12}$-$C_{18}$-alkyldimethylamine oxide, fatty acid amidoalkyldimethylamine oxide.

The hair care preparations according to the invention can additionally contain further additives customary in hair care such as for example perfumes, colorants, also those which simultaneously dye or tint the hair, solvents, opacifying agents and pearly luster agents, for example esters of fatty acids with polyols, magnesium and zinc salts of fatty acids, dispersions based on copolymers, thickening agents such as sodium, potassium and ammonium chloride, sodium sulfate, fatty acid alkylolamides, cellulose derivatives, natural rubbers, also plant extracts, protein derivatives such as gelatin, collagen hydrolysates, polypeptides with a natural or synthetic basis, egg yolk, lecithin, lanolin and lanolin derivatives, fats, oils, fatty alcohols, silicones, deodorizing agents, substances with antimicrobial activity, substances with antiseborrhoeic activity, substances with keratolytic and keratoplastic effect, such as, for example, sulfur, salicylic acid and enzymes as well as further anti-dandruff agents such as olamine, climbazol, zink pyrithion, ketoconazole, salicylic acid, sulfur, tar preparations, derivatives of undecenic acid, extracts of nettel, rosmary, cottonwood, birch, walnut, willow bark and/or *arnica*.

As the compositions according to the present invention are particularly suitable to treat dandruff, the present invention also relates to a method of treating the scalp, said method comprising the steps of contacting the scalp with a hair care preparation comprising erythrulose and hydroxyacetophenone. In a preferred embodiment the method is directed to the treatment of dandruff. In another preferred embodiment, the hair care preparation is a rinse off composition in the form of a shampoo or a conditioner. In a further preferred embodiment, the method furthermore comprises the step of rinsing the hair with water.

The shampoos are produced in a manner known per se by mixing the individual components and where necessary further processing appropriate for the particular type of preparation.

Examples of hair care preparations in which the combination of erythrulose and hydroxacetophenone can be used according to the invention and which may be mentioned are hair conditioners, hair tonics and hair regenerating compositions, which are rinsed off from the hair after a certain time or, depending on the formulation, can also remain on the hair.

All these preparations are also produced as already mentioned for the shampoo in a manner known per se with the addition of the combination of erythrulose and hydroxacetophenone.

Particular suitable hair care preparations according to the present invention are shampoo preparations comprising (i) erythrulose in an amount selected in the range of 0.005 to 1.0 wt.-%, preferably in the range of 0.01 to 0.8 wt.-%, most preferably in the range of 0.04 to 0.75 wt.-%, based on the total weight of the composition, (ii) p-hydroxacetophenone in an amount selected in the range of about 0.01 wt.-% to 2 wt.-%, preferably in the range of 0.1 wt.-% to 1 wt.-%, most preferably in the range of 0.1 wt.-% to 0.6 wt.-%, based on the total weight of the composition, (iii) water and (vi) at least one anionic surfactant. Preferably, the anionic surfactant is selected from the group consisting of sodium lauryl sulfate, ammonium lauryl sulfate, sodium lauryl ether sulfate, ammonium lauryl ether sulfate, sodium lauroyl sarconisate, sodium oleylsuccinate, ammonium lauryl sulfosuccinate, sodium dodecylbenzol sulfonate and/or triethanolamine dodecylbenzol sulfonate or mixtures thereof, such as in particular sodium lauryl sulfate, ammonium lauryl sulfate, sodium lauryl ether sulfate and/or ammonium lauryl ether sulfate. The total amount of the anionic surfactant in the compositions according to the invention ranges from 0.5 to 45 wt.-%, preferably from 1.5 to 35 wt.-%, more preferably from 7 to 25 wt.-%, in particular from 7 to 15 wt.-% based on the total weight of the composition.

Particular suitable hair conditioners according to the present invention may be rinse off or leave on conditioners, preferably rinse-off conditioners. Particular advantageous hair conditioners according to the present invention comprise ((i) erythrulose in an amount selected in the range of 0.005 to 1.0 wt.-%, preferably in the range of 0.01 to 0.8 wt.-%, most preferably in the range of 0.04 to 0.75 wt.-%, based on the total weight of the composition, (ii) p-hydroxacetophenone in an amount selected in the range of about 0.01 wt.-% to 2 wt.-%, preferably in the range of 0.1 wt.-% to 1 wt.-%, most preferably in the range of 0.1 wt.-% to 0.6 wt.-% based on the total weight of the composition, (iii) water and (iv) at least one conditioning agent such as e.g. silicone oils, quaternary polymers, naturally derived conditioning agents without being limited thereto.

The quaternary polymer is preferably selected from e.g. Polyquaternium-6 (e.g. commercialized under the trade name TILAMAR® Quat 640 or 641), Polyquaternium-22 (e.g. commercialized under the trade name TILAMAR® Quat 2240 or 2241), Polyquaternium-7 (e.g. commercialized under the trade name TILAMAR® Quat 710, 711 or 712), etc, The naturally derived conditioning agents are preferably selected from e.g. sugar based polymers such as Guar Hydroxypropyltrimonium Chloride (e.g. commercialized under the trade name Jaguar C-17, Jaguar C-1000, Jaguar C-13S)), but not limited hereto. In principal, any silicone oil is suitable for use in the hair conditioner. However, the silicone oil is preferably selected from dimethicones, dimethiconols, polydimethylsiloxanes, arylated silicones, cyclic silicones, silicone surfactants and aminated silicones and may be volatile or non-volatile. Particular suitable silicone oils are dimethicone, dimethiconol, polydimethylsiloxane which are available from various suppliers such as Dow Corning. The total amount of the at least one silicone oil in the hair conditioner is preferably selected is in the range of 0.01 to 10 wt.-%, preferably 0.02 to 7.5 wt.-%, more preferably 0.05 to 5 wt.-% and most preferably 0.1 to 3 wt.-%, based on the total weight of the composition.

In another preferred embodiment, the cosmetic compositions according to the present invention are O/W emulsions, W/O emulsions and/or gels such as shower gels or hair gels.

The O/W emulsions according to the present invention advantageously comprise (i) erythrulose in an amount selected in the range of 0.005 to 1.0 wt.-%, preferably in the range of 0.01 to 0.8 wt. %, most preferably in the range of 0.04 to 0.75 wt.-%, based on the total weight of the composition, (ii) p-hydroxacetophenone in an amount selected in the range of about 0.01 wt.-% to 2 wt.-%, preferably in the range of 0.1 wt.-% to 1 wt.-%, most preferably in the range of 0.1 wt.-% to 0.6 wt.-%, based on the total weight of the composition, (iii) water and (iv) at least one O/W- or Si/W-emulsifier selected from the list of glycerylstearatcitrate, glycerylstearate (self emulsifying), stearic acid, salts of stearic acid, polyglyceryl-3-methylglycosedistearate, ceteareth-20, steareth-2, steareth-12, PEG-40 stearate, phosphate esters and the salts thereof such as cetyl phosphate (Amphisol® A), diethanolamine cetyl phosphate (Amphisol® DEA), potassium cetyl phosphate (Amphisol® K), sodiumcetearylsulfat, sodium glyceryl oleate phosphate, hydrogenated vegetable glycerides phosphate, sorbitan oleate, sorbitan sesquioleate, sorbitan isostearate, sorbitan trioleate, lauryl glucoside, decyl glucoside, sodium stearoyl glutamate, sucrose polystearate and Hydrated Polyisobuten as well as mixtures thereof. Also, one or more synthetic polymers may be used as an emulsifier such as for example, PVP eicosene copolymer, acrylates/C10-3o alkyl acrylate crosspolymer, acrylates/steareth-20 methacrylate copolymer, PEG-22/dodecyl glycol copolymer, PEG-45/dodecyl glycol copolymer, and mixtures thereof. In a particular preferred embodiment the 0/W-emulsifier is selected from the group of cetyl phosphates such as in particular potassium cetyl phosphate (commercially available as Amphisol® K), glyceryl stearate (and) PEG 100 stearate (commercially available as Arlacel® 165) and/or polyalkylenglycolether such as in particular laureth-35 (lauryl alcohol with 35 EO units; commercially available as Brij® 35). The at least one 0/W emulsifier is preferably used in an amount of about 0.001 to 10 wt.-%, more preferably in an amount of 0.1 to 7 wt.-% with respect to the total weigh of the composition. Additionally, the cosmetic composition in the form of a O/W emulsion contains advantageously at least one co-emulsifier selected from the list of alkyl alcohols such as Cetyl Alcohol (Lorol C16, Lanette 16) Cetearyl Alcohol (Lanette® 0), Stearyl Alcohol (Lanette® 18), Behenyl Alcohol (Lanette® 22), Glyceryl Monostearate, Glyceryl Myristate (Estol® 3650), Hydrogenated Coco-Glycerides (Lipocire Na10) without being limited to this and mixtures thereof.

The W/O emulsions according to the present invention advantageously comprise (i) erythrulose in an amount selected in the range of 0.005 to 1.0 wt.-%, preferably in the range of 0.01 to 0.8 wt.-%, most preferably in the range of 0.04 to 0.75 wt.-%, based on the total weight of the composition, (ii) p-hydroxacetophenone in an amount selected in the range of about 0.01 wt.-% to 2 wt.-%, preferably in the range of 0.1 wt.-% to 1 wt.-%, most preferably in the range of 0.1 wt.-% to 0.6 wt.-%, based on the total weight of the composition, (iii) water and (iv) at least one W/O- or W/Si-emulsifier selected from the list of polyglyceryl-2-dipolyhydroxystearat, PEG-30 dipolyhydroxystearat, cetyl dimethicone copolyol, polyglyceryl-3 diisostearate polyglycerol esters of oleic/isostearic acid, polyglyceryl-6 hexaricinolate, polyglyceryl-4-oleate, polygylceryl-4 oleate/ PEG-8 propylene glycol cocoate, magnesium stearate, sodium stearate, potassium laurate, potassium ricinoleate, sodium cocoate, sodium tallowate, potassium castorate, sodium oleate, and mixtures thereof. Further suitable W/Si-emulsifiers are Lauryl Polyglyceryl-3 Polydimethylsiloxyethyl Dimethicone and/or PEG-9 Polydimethylsiloxyethyl Dimethicone and/or Cetyl PEG/PPG-10/1 Dimethicone and/ or PEG-12 Dimethicone Crosspolymer and/or PEG/PPG-18/18 Dimethicone. The at least one W/O emulsifier is preferably used in an amount of about 0.001 to 10 wt.-%, more preferably in an amount of 0.2 to 7 wt.-% with respect to the total weigh of the composition.

The gel preparations according to the present invention advantageously comprise (i) erythrulose in an amount selected in the range of 0.005 to 1.0 wt.-%, preferably in the range of 0.01 to 0.8 wt.-%, most preferably in the range of 0.04 to 0.75 wt.-%, based on the total weight of the composition, (ii) p-hydroxacetophenone in an amount selected in the range of about 0.01 wt.-% to 2 wt.-%, preferably in the range of 0.1 wt.-% to 1 wt.-%, most preferably in the range of 0.1 wt.-% to 0.6 wt.-%, based on the total weight of the composition, (iii) water and (iv) at least one water soluble thickener. Such water-soluble thickeners are well known to a person skilled in the art and are e.g. listed in the "Handbook of Water soluble gums and resins" by Robert L. Davidson (Mc Graw Hill Book Company (1980)). Particularly suitable water soluble thickeners are selected from the group consisting of polyacrylic acids (e.g. commercially available under the tradename Carbomer or Carbopol®), homopolymers of 2-Acrylamido-2-methylpropansulfonic acid (e.g. commercially available as Rheothik®11-80), acrylate copolymers (e.g. commercially available under the tradename Pemulen® or Aculyn® 33), branched Poly(methacryloyloxyethyltrimethylammoniumchlorid) (INCI-name Polyquaternium-37), non-modified guar gums (e.g. commercially available under the tradename Jaguar), starch or derivatives thereof and/or hydroxyalkylcellulosen. Preferably the water-soluble thickener is used in an amount of about 0.001 to 10 wt.-%, more preferably in an amount of 0.2 to 7 wt.-%, based on the total weigh of the composition.

The following examples are provided to further illustrate the compositions and effects of the present invention. These examples are illustrative only and are not intended to limit the scope of the invention in any way.

EXAMPLE 1: ANTIMICROBIAL EFFICACY

Actives: Erythrulose from DSM Nutritional products
SymSave® H from Symrise (p-Hydroxyacetophenone)

The antimicrobial efficacy is assessed in analogy to the regulatory challenge test method (NF EN ISO11930). Thus, solutions of the respective active(s) in physiological serum with 0.85 wt.-% NaCl in the concentrations as outlined in the tables below were prepared under sterile conditions. The solutions of the active(s) were then deposed in 96-deep well plates (1.6 ml/well). The wells were contaminated with

*Malassezia furfur, Propionibacterium acnes*, respectively *Aspergillus brasiliensis* to obtain the initial contamination as outlined in table 1, 2 and 3. After contamination, each well was thoroughly mixed to ensure a homogeneous distribution of the microbes. Then each plate was incubated at 22° C. for 24 h. The counting of the (remaining) population was carried out 24 h after contamination. The results are outlined in the tables below.

TABLE 1

Results obtained with *Malassezia furfur*

| # | Test solution | Time [h] | *Malassezia furfur* colony count [cfu/ml] | Δ* |
|---|---|---|---|---|
| 1a | 0.5 wt.-% Erythrulose° | 0 | 3300 | |
| 1b | | 24 | 3300 | ±0% |
| 2a | 0.5 wt.-% p-Hydroxyacetophenone | 0 | 3300 | |
| 2b | | 24 | 550 | −83% |
| 3a | 0.5 wt.-% Erythrulose° | 0 | 3300 | |
| 3b | 0.5 wt.-% p-Hydroxyacetophenone⁺ | 24 | 0 | −100% |

*Δ = ({microorganism count t = 0 h} − {microorganism count t = 24}/{microorganism count t = 0}) * 100
°corresponds to 0.4 wt.-% of active As can be seen in the table above erythrulose at a concentration of 0.5% does not exert any anti-fungal effect against *Malassezia furfur*, which would result in a reduction thereof. However, erythrulose is able to boost the efficacy of p-hydroxyacetophenone against *Malassezia furfur*, when combined therewith.

TABLE 2

Results obtained with *Propionibacterium acnes*

| Test solution | Time [h] | *P. acnes* colony counts [cfu/ml] | Δ* [%] |
|---|---|---|---|
| 0.5 wt.-% Erythrulose° | 0 | 500000 | |
| 0.5 wt.-% p-Hydroxyacetophenone⁺ | 24 | 3 | −100% |

°corresponds to 0.4 wt.-% of active. *Δ = ({microorganism count t = 0 h} − {microorganism count t = 24}/{microorganism count t = 0}) * 100

As can be retrieved from table 2, the combination of erythrulose and p-hydroxyacetophenone is highly active against *P. acnes*.

TABLE 2

Results obtained with *Aspergillus brasiliensis*

| Test solution | Time [h] | *Aspergillus brasiliensis* colony count [cfu/ml] | Log step reduction |
|---|---|---|---|
| 0.5 wt.-% Erythrulose° | 0 | 10000 | |
| | 24 | 100 | 2 |
| 0.4 wt.-% p-Hydroxyacetophenone | 0 | 10000 | |
| | 24 | 100 | 2 |
| 0.25 wt.-% Erythrulose* 0.2 wt.-% p-Hydroxyacetophenone | 0 | 10000 | |
| | 24 | 0 | 4 |

°corresponds to 0.4 wt.-% of active
*corresponds to 0.2 wt.-% of active (The term "Log reduction" is a well-known mathematical term used to show the relative number of cells, germs, microbes, etc., reduced in or on something, e.g. a 2 log reduction means the number of microbes is 100 times smaller and a 3 log reduction means the number of microbes is 1000 times smaller).

As can be seen in table 3 the combination of erythrulose and hydroxyacetophenone shows a synergistic effect against *Aspergillus brasiliensis*.

EXAMPLE 2: O/W FOUNDATION

| Ingredients | INCI | wt. % |
|---|---|---|
| Deionised Water | Aqua | Ad 100 |
| Glycerin | Glycerin | 2.00 |
| Triethanolamine | Triethanolamine | 0.80 |
| Paratexin | Methylparaben EP | 0.20 |
| Keltrol | Xanthan Gum | 0.30 |
| Erythrulose | Erythrulose | 0.5 |
| Titanium dioxide | C.I. 77891 | 4.57 |
| SunCROMA yellow iron oxide | C.I. 77492 | 0.30 |
| SunCROMA red iron oxide | C.I. 77491 | 0.13 |
| SunCROMA black iron oxide | C.I. 77499 | 0.20 |
| DC 556 | Phenyl Trimethicone | 3.60 |
| Stearic Acid | Stearic Acid | 1.4 |
| Cetyl Alcohol | Cetyl Alcohol | 3.0 |
| Paratexin P | Propylparaben EP | 0.1 |
| p-Hydroxyacetophenone | Hydroxyacetophenone | 0.5 |

EXAMPLE 3: ALCOHOL FREE FACIAL TONIC

| Ingredients | INCI | wt. % |
|---|---|---|
| Polysorbate 20 | Polysorbate 20 | 2.00 |
| Alpaflor Calendula AO | *Calendula Officinalis* Extract, Glycerin, Water | 0.80 |
| Alpaflor Buddleja AO | *Buddleja Davidii* Extract, Glycerin, Water | 0.80 |
| Ariasilk Phospholipd CDM | Sodium Coco PG-Dimonium Chloride Phosphate | 0.50 |
| Fragrance | Parfum | 0.10 |
| Deionised Water | Aqua | Ad 100 |
| Citric Acid | Citric Acid | 0.01 |
| Erythrulose | Erythrulose | 0.75 |
| Paratexin FRP | Ethylparaben, Butylparaben, Propylparaben, Isobutylparaben | 0.10 |
| p-Hydroxyacetophenone | Hydroxyacetophenone | 0.7 |

EXAMPLE 4: W/O CREAM

| Ingredients | INCI | wt. % |
|---|---|---|
| Cremophor WO-7 | PEG-7 Hydrogenated Castor Oil | 2.50 |
| Elfacos ST-9 | PEG-45/Dodecyl Glycol Copolymer | 2.00 |
| Cirebelle 303 | Synthetic Wax | 5.00 |
| Cirebelle 109L | Synthetic Wax | 7.20 |
| Miglyol 818 | Caprylic/Capric/Linoleic Triglyceride | 5.00 |
| Eutanol G | Octyldodecanol | 7.50 |
| Cetiol OE | Dicaprylyl Ether | 9.20 |
| Deionised Water | Aqua | Ad 100 |
| Glycerin | Glycerin | 5.00 |
| Propylene Glycol | Propylene Glycol | 2.00 |
| Euxyl PE 9010 | Phenoxyethanol and Ethylhexylglycerin | 0.80 |
| Erythrulose | Erythrulose | 0.3 |
| p-Hydroxyacetophenone | Hydroxyacetophenone | 0.1 |

EXAMPLE 5: SOOTHING GEL

| Ingredients | INCI | wt. % |
|---|---|---|
| Deionised Water | Aqua | Ad 100 |
| Keltrol CG RD | Xanthan Gum | 0.50 |
| Sodium Benzoate | Sodium Benzoate | 0.20 |
| Potassium Sorbate | Potassium Sorbate | 0.25 |
| Alpaflor *Marrabium* AO | Glycerin, Aqua, *Marrubium Vulgare*, Sodium Benzoate, Potassium Sorbate | 3.00 |
| Erythrulose | Erythrulose | 0.45 |
| p-Hydroxyacetophenone | Hydroxyacetophenone | 0.65 |

EXAMPLE 6: O/W LOTION

| Ingredients | INCI | wt. % |
|---|---|---|
| Deionised Water | Aqua | Ad 100 |
| Menthol | Menthol | 0.10 |
| Keltrol CG SFT | Xanthan Gum | 1.25 |
| Ceralution ES | Ceteareth-25, Di Sodium Ethylene Dicocamide PEG-15 Disulfate | 2.00 |
| Isofol 20 | Octyldodecanol | 5.00 |
| Paratexin EC5 | Benzoic Acid Benzyl Alcohol, Dehydroacetic Acid, Sorbic Acid | 1.00 |
| Erythrulose | Erythrulose | 0.4 |
| p-Hydroxyacetophenone | Hydroxyacetophenone | 0.3 |

EXAMPLE 7: FACIAL CLEANSING GEL

| Ingredients | INCI | wt. % |
|---|---|---|
| Deionised Water | Aqua | Ad 100 |
| Carbopol AQUA SF-1 Polymer | Acrylates Copolymer | 7.50 |
| Texapon NSO-BZ | Sodium Laureth Sulfate | 41.00 |
| Miranol Ultra C 32 | Sodium Cocoamphoacetate | 5.00 |
| Hostapon CLG | Sodium Lauroyl Glutamate | 4.50 |
| Jaguar C 162 | Hydroxypropyl Guar Hydroxypropyltrimonium Chloride | 1.00 |
| Erythrulose | Erythrulose | 0.3 |
| Euxyl K 300 | Phenoxyethanol & Methylparaben & Propylparaben & Ethylparaben & Butylparaben & Isobutylparaben | 0.80 |
| Alpaflor *Malvia* AO | Glycerin, Aqua, *Malva Sylvestris* (Mallow) Flower Extract, Potassium Sorbate, Sodium Benzoate | 2.00 |
| Parfum Limette | Fragrance | q.s. |
| FD&C Yellow 5 | CI 19140 | 0.50 |
| Frescolat Plus | Menthyl Lactate, Menthol | 0.20 |
| Dehyton AB-30 | Coco Betaine | 2.00 |
| Rewoderm LI S 80 | PEG-200 Hydrogenated Glyceryl Palmate & PEG-7 Glyceryl Cocoate | 1.00 |
| Citric Acid | Citric Acid | q.s. |
| p-Hydroxyacetophenone | Hydroxyacetophenone | 0.5 |

EXAMPLE 8: LEAVE-ON HAIR AND SCALP CONDITIONER

| Ingredients | INCI | wt. % |
|---|---|---|
| Deionised Water | Aqua | Ad 100 |
| Ethanol DEB 96 | Alcohol denat. | 30.00 |
| PVP/VA Copolymer | PVP/VA Copolymer | 2.50 |
| Euxyl K-300 | Phenoxyethanol, Methylparaben, Butylparaben, Ethylparaben, Propylparaben, Isobutylparaben | 0.80 |
| Protachem HCO-40 | PEG-40 Hydrogenated Castor Oil | 0.50 |
| Fragrance ADAM | Parfum | 0.10 |
| Triethanolamine 99% | Triethanolamine | 0.01 |
| FD & C Yellow No 5 (0.5% Solution) | CI 19140, Aqua | 0.10 |
| FD & C Blue No 1 (0.5% Solution) | CI 42090, Aqua | 0.10 |
| Erythrulose | Erythrulose | 0.1 |
| p-Hydroxyacetophenone | Hydroxyacetophenone | 0.3 |

EXAMPLE 9: SHAMPOO

| INCI Nomenclature | wt. % |
|---|---|
| Aqua (water) | Ad 100 |
| Ammonium laureth sulfate | 10.00 |
| Ammonium lauryl sulfate | 5.00 |
| Glycol distearate | 1.00 |
| Dimethicone | 1.00 |
| Cetyl alcohol | 0.50 |
| Cocamide MEA | 3.00 |
| Erythrulose | 0.8 |
| ZPT | 0.50 |
| Guar hydroxypropyltrimonium chloride | 0.20 |
| Hydrogenated polydecene | 1.00 |
| Polyquaternium 10 | 0.30 |
| PEG 7m | 0.50 |
| Trimethylpropane tricaprylate/tricaprate | 1.00 |
| Preservative | q.s. |
| Fragrance | 0.30 |
| E 104, E 110, E 132 | 0.02 |
| p-Hydroxyacetophenone | 0.7 |

EXAMPLE 10: CLEAR SHAMPOO WITH PLANT EXTRACTS

| INCI Nomenclature | wt. % |
|---|---|
| Aqua (water) | Ad 100 |
| Sodium laureth sulfate | 10.00 |
| Lauryl glucoside | 6.00 |
| Cocamidopropyl betaine, | 2.00 |
| Propylene glycol | 2.00 |
| Perfume oil | 1.25 |
| Sodium citrate | 0.25 |
| Sodium benzoate | 0.20 |
| Panthenol | 1.00 |
| Sodium formate | 0.20 |
| Polyquaternium-10 | 0.20 |
| Hydroxypropyl guar hydroxypropyltrimonium chloride | 0.05 |
| Erythrulose | 0.2 |
| PEG-35 castor oil | 1.00 |
| Maris sal | 1.25 |
| Polysorbate 20 | 1.00 |
| Tocopheryl acetate | 0.20 |
| *Prunus armeniaca* | 0.20 |
| *Echinacea purpurea* | 0.05 |
| Tocopherol | 0.05 |
| Linoleic acid | 0.20 |
| Preservative | 1.00 |
| CI77891 | 0.02 |
| p-Hydroxyacetophenone | 0.6 |

EXAMPLE 11: RINSE-OFF HAIR AND SCALP CONDITIONER

| INCI Nomenclature | wt. % |
|---|---|
| Aqua (water) | Ad 100 |
| Stearyl alcohol | 2.50 |
| Cetyl alcohol | 2.50 |
| Behentrimonium chloride | 1.30 |
| Dimethicone | 2.00 |
| Erythrulose | 0.3 |
| Fragrance | 0.50 |
| Butylene glycol | 2.00 |
| Methyl parabene | 0.30 |
| p-Hydroxyacetophenone | 0.3 |

The invention claimed is:

1. A topical composition comprising erythrulose and from 0.01 wt. % to 2 wt. %, based total weight of the composition, of hydroxyacetophenone.

2. The topical composition according to claim 1, wherein the erythrulose is present in an amount from 0.005 to 5 wt. %, based on the total weight of the composition.

3. The topical composition according to claim 1, wherein the hydroxyacetophenone is p-hydroxyacetophenone.

4. The topical composition according to claim 1, wherein the composition is a cosmetic or pharmaceutical composition.

5. The topical composition according to claim 4, wherein the composition is a shampoo preparation, a hair conditioner, an oil-in-water (O/W) emulsion, a water-in-oil (W/O) emulsion or a gel.

6. The topical composition according to claim 1, wherein the composition further comprises water and at least one agent selected from the group consisting of surfactants, emulsifiers, thickeners and oils.

7. The topical composition according to claim 1, wherein the hydroxyacetophenone is present in an amount from 0.1 wt. % to 1 wt. %, based on the total weight of the composition.

8. The topical composition according to claim 1, wherein the hydroxyacetophenone is present in an amount from 0.1 wt. % to 0.6 wt. %, based on the total weight of the composition.

9. The topical composition according to claim 1, wherein the erythrulose is present in an amount from 0.01 to 3 wt. %, based on the total weight of the composition.

10. The topical composition according to claim 1, wherein the erythrulose is selected is present in an amount from 0.025 to 2 wt. %, based on the total weight of the composition.

11. A method of treating skin and/or scalp which comprises contacting the skin and/or scalp with the topical composition according to claim 1.

12. The method according to claim 11, wherein the method is for the treatment, prevention and/or prophylaxis of itching skin and/or for maintaining a healthy skin homeostasis and/or for maintaining skin microbiome balance.

13. A method for the treatment of itching skin and/or for maintaining a healthy skin homeostasis and/or for maintaining skin microbiome balance, wherein the method comprises topically applying to skin an effective amount of the topical composition according to claim 1.

14. The method according to claim 13, wherein the method is for the treatment, prevention and/or prophylaxis of *Malassezia* yeast.

15. The method according to claim 14, wherein the *Malassezia* yeast comprises *Malassezia* furfur.

16. The method according to claim 15, wherein the diseases and/or disorders are selected from the group consisting of *pityriasis versicolor*, dandruff formation, seborrheic dermatitis, atopic dermatitis and psoriasis.

17. A method for the prevention and/or prophylaxis of acne, wherein the method comprises topically applying to skin an amount of the topical composition according to claim 1 sufficient to provide prevention and/or prophylaxis of acne.

* * * * *